United States Patent
Schultz et al.

(10) Patent No.: US 10,191,028 B1
(45) Date of Patent: *Jan. 29, 2019

(54) INORGANIC NANOPARTICLE MATRICES FOR SAMPLE ANALYSIS

(75) Inventors: John Albert Schultz, Houston, TX (US); Michael V. Ugarov, Houston, TX (US)

(73) Assignee: Ionwerks, Houston, TX (US)

( * ) Notice: Subject to any disclaimer, the term of this patent is extended or adjusted under 35 U.S.C. 154(b) by 2319 days.

This patent is subject to a terminal disclaimer.

(21) Appl. No.: 10/861,970

(22) Filed: Jun. 4, 2004

Related U.S. Application Data (60) Provisional application No. 60/476,718, filed on Jun. 6, 2003.

(51) Int. Cl.
*G01N 33/483* (2006.01)
*H01J 49/16* (2006.01)

(52) U.S. Cl.
CPC ........ *G01N 33/4833* (2013.01); *H01J 49/164* (2013.01)

(58) Field of Classification Search
CPC .......................... G01N 33/4833; H01J 49/164
USPC ............. 435/174, 176, 177, 180–182, 287.7, 435/287.9, DIG. 9, DIG. 11, DIG. 12, 435/DIG. 14, DIG. 15, DIG. 17, DIG. 19; 436/518, 524, 525, 528, 531, 532, 535, 436/173, 174; 204/157.61, 157.65, 204/158.14; 250/288; 264/4.6; 516/901; 423/445 B; 422/245.1; 257/53, 55, 257/E51.045; 252/501.1, 502, 503, 252/506–509, 510, 408.1, 600; 210/702, 210/710; 118/58; 438/510, 535, 900, 438/914, 962, 971, 974; 585/812, 817; 159/DIG. 11; 427/541, 903; 376/183; 977/736, 738, 739

See application file for complete search history.

(56) References Cited

U.S. PATENT DOCUMENTS

| | | | |
|---|---|---|---|
| 5,959,297 A | * 9/1999 | Weinberg et al. | 250/288 |
| 6,004,617 A | * 12/1999 | Schultz et al. | 506/15 |
| 6,121,624 A | * 9/2000 | Stevie | H01L 21/2652 250/282 |
| 6,162,926 A | * 12/2000 | Murphy et al. | 548/417 |
| 6,558,902 B1 | 5/2003 | Hillemkamp | |

(Continued)

FOREIGN PATENT DOCUMENTS

| EP | 0546718 A2 | * 6/1993 |
|---|---|---|
| WO | WO 03/021267 | * 3/2003 |

OTHER PUBLICATIONS

Michalak et al., C60 assisted laser desorption-ionization mass spectrometry, 1995, FIZIKA A, 4(2):pp. 321-327.*

(Continued)

*Primary Examiner* — Scott Long
*Assistant Examiner* — Gary E Hollinden
(74) *Attorney, Agent, or Firm* — Norton Rose Fulbright US LLP (57) ABSTRACT

A new type of matrices for Matrix Assisted Laser Desorption and Ionization technique based on derivatized carbon clusters, which will be suitable for the analysis of peptides, proteins and other biomolecules by mass spectrometry which has several advantages over conventional matrices, such as optical sensitivity in a broad spectrum, low interference in the wide mass range and high analyte ionization efficiency.

21 Claims, 7 Drawing Sheets

(56) References Cited

U.S. PATENT DOCUMENTS

| | | | |
|---|---|---|---|
| 6,624,409 B1 | 9/2003 | Mordehai et al. | |
| 6,639,213 B2 | 10/2003 | Gillig et al. | |
| 6,683,299 B2 | 1/2004 | Fuhrer et al. | |
| 6,802,456 B2* | 10/2004 | Shekarriz et al. | 239/3 |
| 6,821,730 B2 | 11/2004 | Hannah | |
| 7,202,472 B2* | 4/2007 | Schmucker et al. | 250/288 |
| 2001/0032929 A1 | 10/2001 | Fuhrer et al. | |
| 2002/0034827 A1* | 3/2002 | Singh et al. | 436/177 |
| 2002/0094533 A1* | 7/2002 | Hess | B01J 19/0046 435/6.14 |
| 2003/0022225 A1* | 1/2003 | Monforte et al. | 435/6 |
| 2004/0091498 A1* | 5/2004 | Zhang et al. | 424/185.1 |
| 2004/0214236 A1* | 10/2004 | Brines et al. | 435/7.2 |
| 2005/0035284 A1* | 2/2005 | Schultz | H01J 49/0031 250/287 |
| 2005/0230615 A1* | 10/2005 | Furutani et al. | 250/287 |
| 2005/0277201 A1* | 12/2005 | Sivarajan et al. | 436/173 |

OTHER PUBLICATIONS

Brown et al., Matrix-assisted laser desorption/ionization of amphiphilic fullerene derivatives, 2001, Int J Mass Spec, 210/211: pp. 249-263.*

Felder et al., Syntehsis of amphiphilic fullerene derivatives and their incorporation in Langmuir and Langmuir-Blodgett films, 2002, Hely Chim Acta, 85: pp. 288-319.*

Langen et al., From genome to proteome: protein map of Haemophilus influenzae, 1997, 18: pp. 1184-1192.*

Huang et al., Polyfunctional fullerene derivatives as UV-MALDI matrices to detect peptides and proteins, 1999, 7(4): pp. 541-550.*

Novikov et al., Matrix-implanted laser desorption/ionization mass spectrometry, 2004, Anal Chem, 76: pp. 7288-7293.*

Goel, a. et al., "Size analysis of single fullerene molecules by electron microscopy", Carbon (2004) 42:1907-1915.*

Troendle et al., "Detection of Pharmaceutical Compounds in Tissue by Matrix-Assisted Laser Desorption/Ionization and Laser Desorption/ Chemical Ionization Tandem Mass Spectrometry with a Quadrupole Ion Trap", J Am Soc Mass Spectrometry (1999), 10:1315-1321.*

L. Michalak, K. Fisher, D. Alderdice, G. Willet; OMS Letters—C60 Assisted Laser Desorption-Ionization Mass Spectrometry; Rapid Commun. Org. Mass Spectrom. 29, 512 (1994).

F. Hopweed, L. Michalak, D. Alderdice, K. Fisher, G. Willet; C60-Assisted Laser Desorption/Ionization Mass Spectrometry in the Analysis of Phosphotungstic Acid; Mass Spectrom. 8, 881 (1994).

J. Huang, L. Wang, L. Chiang, J. Shiea; Polyfunctional Fullerene Derivatives as UV-MALDI Matrices to Detect peptides and Proteins; J. Fullerene Sci. Technol. 7, 541 (1999).

J. Shiea, J. Huang, C. Teng, J. Jeng, L. Wang, L. Chiang; Use of a Water-Solubel Fullerene Derivative as Precipitating Reagent and Matrix-Assisted Laser Desorption/Ionization Matrix to Selectively Detect Charged Species in AAqueous Solutions; Anal. Chem. 75, 3587 (2003).

T. Brown, N. Clipston, N. Simjee, H. Luftmann, H. Hungerbuhler, T. Drewello; Matrix-assisted laser desorption/ionization of amphiphilic fullerene derivatives; Inter. J. Mass Spectrom. 210/211, 249-263 (2001).

R. Beck, P. Weis, A. Hirsch, I. Lamparth; Laser Desorption Mass Spectrometry of Fullerene Derivatives: Laser-Induced Fragmentation and Coalescence Reactions; Phys. Chem. 98, 9683-9687 (1994).

Tecklenburg, R.E., Jr.; Russell, D.H.; An evaluation of the analytical utility of the photodissociation of fast ion beams; Mass Spectrom. Rev., 9, 405-451 (1990).

Amina S. Woods, Michael Ugarov, Tom Egan, John Koomen, Kent J. Gillig, Katrin Fuhrer, Marc Gonin, and J. Albert Schultz; Lipid/ Peptide/Nucleotide Separation with MALDI-Ion Mobility-TOF MS; Anal. Chem., 76, 2187 (2004).

Michael V. Ugarov, T. Egan, Dmitry V. Khabashesku, J. Albert Schultz, Haiqing Peng, Valery N. Khabashesku, Hiroshi Furutani, Kimberley S. Prather, H-W. J. Wang, S. N. Jackson, and Amina S. Woods, MALDI matrices for biomolecular analysis based on functionalized carbon nanomaterials, Anal. Chem.; 2004, 76 (22) 6734-6742.

Karas M., Bachman D., Hillenkamp F.; Matrix-Assisted Ultraviolet Laser Desorption of Non-Volatile Compounds; Int J. Mass Spectrrom. Ion Processes 1987, 78, (53).

Schurenberg M., Dreisewerd K., and Hillenkamp F.,"Laser Desorption/ Ionization Mass Spectrometry of Peptides and Proteins with Particle Suspension Matrixes," Anal. Chem. 1999, 71 (221-229).

K.J. Gillig, B. Rutolo, E.G. Stone, D.H. Russell, K. Fuhrer, M. Gonin, J.A. Schultz, "Coupling High Pressure MALDI with Ion Mobility Orthogonal Time-of-Flight Mass Spectromerry," Anal. Chem. p. 72, 3965, (2000).

A.S. Woods, J. Koomen, B. Ruotolo, K.J. Gillig, D.H. Russell; K. Fuhrer, M. Gonin, T. Egan and J.A. Schultz,; A Study of Peptide-peptide Interactions Using MALDI Ion Mobility o-TOF and ESI-TOF Mass Spectrometry, J. Amer. Soc. Mass Spectr. 2002, 13 (166-169).

Pierre Chaurand and Richard M. Caprioli; Direct profiling and imaging of peptides and proteins from mammalian cells and tissue sections by mass spectrometry; Electrophoresis 2002, 23, 3125-3155.

A. Brunelle, S. Della-Negra, J. Depauw, D. Jacquet, Y. Lebeyec, M. Pautrat, K. Baudin, H.H. Andersen; Enhanced secondary-ion emission under gold-cluster bombardment with energies from keV to MeV per atom; Phys. Rev. A 2001, 63, 22902.

Novikov, A., Croff, M.; Della-Negra, S.; Le Beyec, Y.; Pautrat, M.; Schultz, J.A.; Ugarov, M.; Egan, T.; Tempez, A.; Wang, H-Y. J.; Jackson, S.N.; Woods, Matrix-Implanted Laser Desorption/ Ionization Mass Spectrometry, A.S. Anal Chem. 2004, 76,7288-7293.

Tempez, A.; Ugarov, M.; Egan, T.; Schultz, J.A.; Novikov, A.; Della-Negra, S.; Le Beyec, Y.; Pautrat, M.; Caroff, M.; Smetkowski, V.S.; Wang, H-Y. J.; Jackson, S.N.; Woods, A.S., Matrix-Implanted Laser Desorption Ionization (MILDI) combined with ion mobility-mass spectrometry for bio-surface analysis; accepted in J. of Proteom. Res. (p. est: 5.3).

A. Tempez, J.A. Schultz, S. Della-Negra, J. Depauw, D. Jacquet, A. Novikov, Y. Lebeyec, M. Pautrat, M. Caroff, M. Ugarov, H. Bensaoula, M. Gonin, K. Furher, and Amina Woods; Orthogonal time-of-flight secondary iron mass spectrometric analysis of peptides using alrge gold clusters as primary ions; Rapid Commun. Mass Spectrom., 2004, 18, 371-376.

B. Ruotolo, K. Gillig, A. Woods, T. Egan, M. Ugarov, J.A. Schultz, D. Russell; Analysis of Phosphorylated Peptides by Ion Mobility-Mass Spectrometry; Anal Chem., 76, 6727-6733.

S. Jackson, HJ Wang, A. Woods, M. Ugarov, T. Egan, JA Schultz,; Direct Tissue Analysis of Phospholipids in Rat Brain Using MALDI-TOFMS and MARLDI-Ion Mobility-TOFMS; J Am Soc Mass Spectrom 2005, 16, 133-138.

\* cited by examiner

INORGANIC NANOPARTICLE MATRICES FOR SAMPLE ANALYSIS

CROSS-REFERENCE TO RELATED APPLICATIONS

This application claims priority to U.S. provisional application Ser. No. 60/476,718, filed Jun. 6, 2003.

TECHNICAL FIELD

The present invention relates generally to instrumentation for the characterization and analysis of molecular ions based at least on their structures and mass-to-charge ratios as gas-phase ions using an improved MALDI ionization matrix and combining this matrix with a MALDI-Ion Mobility-orthogonal time of flight mass spectrometer. More specifically, to such instrumentation which provides for rapid and sensitive analysis of composition, sequence, and/or structural information relating to organic molecules, including biomolecules, inorganic molecules, and biological fluids and surfaces including blood, urine, saliva, and tissue samples.

BACKGROUND OF THE INVENTION

MALDI (matrix-assisted laser desorption ionization) mass spectrometry of biomolecular ions was first demonstrated in parallel efforts by Tanaka et al. using small metal particles suspended in glycerol and by Karas and Hillenkamp (as well as Tanaka) using small organic acid molecules as matrices. In using either the particle matrices or the small organic acid matrices the matrix performs the dual function of both absorbing the laser light and ionizing the non-light absorbing analyte biomolecules through specific and poorly understood chemical reactions. The particle matrices actually perform yet a third function by physisorbing the analyte from solution onto the particle surface. The organic acid matrices met with greater success in the marketplace in part due to their ease of use over wider applicable mass ranges for proteins and peptides. However, they are not completely free of defects, the most notable being the narrow band optical absorption of the excitation radiation, and the non uniform distributed analyte during the co-crystallization of matrix and analyte, and others.

Efforts to use the slurried small particles has languished in all but a few laboratories primarily because of the fundamental problem that the adsorbed protein must also be surrounded by just the right amount of glycerol (interestingly, while other organics have been used in place of glycerol, none appear to work nearly as well). The drying process to establish the correct amount of glycerol is dynamic under vacuum so that the "right amount" is only transitorily achieved. This leaves just a few minutes at a specific time and place near the edge of the sample droplet for acquisition of good spectra. Nevertheless the small metal particulates, because of their flat optical absorbance over a large range of wavelengths, have a huge potential advantage over organic matrices because in principle a wider variety of lasers can be used to perform the experiments. Shurenberg has reviewed the literature and performed a number of illuminating experiments, all of which establish the current understanding of these nanoparticulate matrices. In summary, up to masses of around 13 kDa for proteins, the particle/glycerol system will give identical spectra as organic acid matrices (though with about an order of magnitude less sensitivity). Above this mass range the slurried particles cannot compete with the performance of chemical matrices. Any refractory particle seems to work—including carbon nanosoot and titanium nitride—as long as the particle size is significantly below 1 micron and as long as glycerol is added.

The first use of fullerenes for laser desorption of biomolecules involved applying the protein analyte solution directly onto the pre-deposited fullerene film (L. Michalak, K. Fisher, D. Alderdice, G. Willet, *Rapid Commun. Org. Mass Spectrom.* 29, 512 (1994); F. Hopweed, L. Michalak, D. Alderdice, K. Fisher, G. Willet, *Mass Spectrom.* 8, 881 (1994)). This technique suffered from low sensitivity and presence of "hot spots" due to poor mixing of a non-polar matrix and a polar analyte. However, the surface polarity of fullerenes can be significantly increased by derivatization with a variety of functional groups. $C_{60}$ functionalized with $(NHC(CH_2OH)_3)_n$, $(C_4H_9SO_3Na)_n$ (see J. Huang, L. Wang, L. Chiang, J. Shiea, *J. Fullerene Sci. Technol.* 7, 541 (1999)), and $((CH_2)_4SO_3)_6$ (see J. Shiea, J. Huang, C. Teng, J. Jeng, L. Wang, L. Chiang, *Anal. Chem.* 75, 3587 (2003)) have been shown to work as matrices for several amino acids, peptides and proteins. High nanomole concentrations of these soluble fullerenes were used either to mix with the analyte solutions or to precipitate specific molecular fractions from mixtures by binding with derivatized fullerenes. A detection limit in the low picomole range was estimated.

Although the MALDI technique has greatly enhanced the art of mass spectrometric analysis of biomolecules, there remains much room for improvement. It would be desirable to develop a particle based MALDI matrix that eliminates the need for glycerol addition and the concomitant problems associated with it. The ideal particle matrix would include an efficient, broadband absorber to allow one to take advantage of electromagnetic radiation sources, especially laser sources operating at wavelengths other than 357 nm from a nitrogen laser, covering a wide range of wavelengths. Work by Hillenkamp and others has used pulsed infrared lasers for MALDI analysis of analytes such as peptides and oligonucleotides codeposited with water. The water acts both as matrix and proton donor and absorbs the pulsed IR laser radiation to allow time of flight mass spectrometry of the desorbed analyte. An efficient particle matrix absorber would also allow one to use low laser power excitation over a wide, nonspecific spectral range. It would also permit the use, by orders of magnitude, of smaller molar ratio of matrix/analyte than is possible now with small organic matrices. Finally, it would be useful to employ such a matrix in a mass spectrometric method having molecular shape selectivity to isobaric matrix interference from the mass spectrum of the analyte.

BRIEF SUMMARY OF THE INVENTION

The present invention is directed to a system and method for the matrix-assisted laser desorption ionization ion mobility and mass spectrometric analysis of elemental and molecular ion species. The following numbered sentences more readily describe the present invention.

In one aspect of the present invention there is a method of preparing an analyte for analysis by laser desorption mass spectrometry, the method comprising the step of: combining the analyte with a matrix, the matrix comprising a native or derivatized fullerene or an inorganic nanoparticle or any combination thereof. In some embodiments, the native or derivatized fullerene is selected from the group consisting of native or derivatized $C_{60}$, native or derivatized $C_{70}$, native or derivatized $C_{76}$, native or derivatized $C_{84}$, and any combination thereof. In some embodiments, the inorganic nanoparticle is selected from the group consisting of nanoparticles of titanium nitride, aluminum nitride, boron nitride, carbonitride, carbon boron nitride, and any combination thereof. In some embodiments, the inorganic nanoparticles comprise metal (the metal may be pure metal, a combination of metals, or metal clusters, the latter being comprised of one or more metal atoms or molecules). In some embodiments, the metal is selected from the group consisting of gold, silver molybdenum, copper, copper lithium alloy, platinum, clusters thereof, and any combination thereof. In some embodiments, the ratio of the matrix to analyte ranges from 10:1 to 1:10000. In some embodiments, the ratio of the matrix to analyte ranges from 1:1 to 1:1000. In some embodiments, the analyte comprises protein. In some embodiments, the protein comprises antibodies or enzymes. In some embodiments, the analyte comprises a component selected from the group consisting of nucleic acids, oligonucleotides, any constituent components thereof, and any combination of the foregoing. In some embodiments, the analyte comprises lipoproteins. In some embodiments, the analyte is a lipid selected from group consisting of phospholipids, ceramides, derivatives thereof, and any combination of the foregoing. In some embodiments, the analyte may comprise a component selected from the group consisting of glycosylated proteins, glycosylated lipids, lipopolysaccharides, glycans, and any combination of the foregoing. In some embodiments, the analyte comprises synthetic organic polymers, synthetic inorganic polymers, or both. In some embodiments, the analyte comprises small organic molecules, organometallic molecules, or both. In some embodiments, the analyte comprises a component selected from the group consisting of herbicides, pesticides, explosives, pharmaceutical drugs, and any combination thereof. In some embodiments, the analyte is a drug of addiction. In some embodiments, the drug of addition is selected from the group consisting of cocaine, morphine, heroin, amphetamine and derivatives thereof. In some embodiments, the derivatized fullerene is derivatized with a chemical moiety. In some embodiments having a chemical moiety, the chemical moiety is selected from the group consisting nicotinic acid, benzoic acid, pyrazinecarboxylic acid, vanillic acid, cinnamic acid, benzyl alcohol, phenol, acetic acid, propionic acid, butyric acid, valeric acid, derivatives thereof, and any combination of the foregoing. In some embodiments, the chemical moiety is selected from the group consisting of ethanol, propanol, butanol, isomers thereof, and any combination of the foregoing. In some embodiments, the matrix comprises components having acid functionalities, alcohol functionalities, or both. In some embodiments, the acid or alcohol functionalities are further functionalized with alkali metal ions. In some embodiments, a quaternary amine is attached by salt formation to the matrix. In some embodiments having a quaternary amine, the quaternary amine is acetylcholine or ammonium hydroxide. In some embodiments, the combined analyte and matrix comprises a solution, and the solution further comprises a buffer. In some embodiments having a derivatized fullerene, the derivatized fullerene comprises a fullerene derivatized on its surface with a peptide sequence. In some embodiments having a derivatized fullerene, the derivatized fullerene comprises a fullerene derivatized on its surface with an epitope. In some embodiments having fullerene, the fullerene is derivatized with a biotin tag. In some embodiments having derivatized fullerene, derivatized fullerene is surface derivatized with acid functionality with long chain fatty acids.

In another embodiment of the present invention, there is a method of preparing an analyte for analysis by laser desorption mass spectrometry, the method comprising the step of: mixing an analyte with matrix, said matrix comprising a native or derivatized fullerene, an inorganic nanoparticle, or a combination thereof; atomizing the mixture to form aerosol droplets; and, depositing the aerosol droplets on a sampling surface. In some embodiments, the analyte and matrix are in separate solutions prior to said mixing step. In some embodiments wherein the analyte and matrix are in separate solutions prior to said mixing step, the separate solutions are both aqueous solutions.

In another embodiment of the present invention, there is a method of preparing an analyte for analysis by laser desorption mass spectrometry, the method comprising the step of combining the analyte with a matrix comprising a native or derivatized nanotube. In some embodiments, the nanotube is a native or derivatized single wall nanotube. In some embodiments, the nanotube is derivatized with a chemical moiety. In some embodiments, the ratio of the matrix to analyte ranges from 10,000:1 to 1:100. In some embodiments, the ratio of the matrix to analyte ranges from 100:1 to 1:100. In some embodiments, the analyte comprises proteins. In some embodiments, the analyte is selected from the group consisting of nucleic acids, oligonucleotides, any constituent components thereof, and any combination of the foregoing. In some embodiments having derivatized fullerene, the derivatized fullerene is derivatized with a chemical moiety. In some embodiments wherein the derivatized fullerene is derivatized with a chemical moiety, the chemical moiety is selected from the group consisting of nicotinic acid, benzoic acid, pyrazinecarboxylic acid, vanillic acid, cinnamic acid, benzyl alcohol, phenol, acetic acid, propionic acid, butyric acid, valeric acid, derivatives thereof, and any combination of the foregoing. In some embodiments, the chemical moiety is selected from the group consisting of ethanol, propanol, butanol, isomers thereof, and any combination the foregoing. In some embodiments, the matrix comprises components having acid functionalities, alcohol functionalities, or both. In some embodiments having acid functionalities, alcohol functionalities or both, the acid or alcohol functionalities are further functionalized with alkali metal ions. In some embodiments, a quaternary amine is attached by salt formation to the matrix. In some embodiments having a quaternary amine attached by salt formation to the matrix, the quaternary amine is acetylcholine or ammonium hydroxide. In some embodiments, the combined analyte and matrix comprises a solution, and said solution further comprises a buffer. In some embodiments having derivatized fullerene, the derivatized fullerene comprises a fullerene derivatized on its surface with a peptide. In some embodiments, the derivatized fullerene comprises a fullerene derivatized on its surface with an epitope. In some embodiments, the fullerene is derivatized with a biotin tag. In some embodiments, the fullerene surface is derivatized with acid functionality with long chain fatty acids.

In another embodiment of the present invention, there is a method of preparing an analyte for analysis by laser desorption mass spectrometry, the method comprising the step of mixing an analyte with matrix, said matrix comprising a native or derivatized nanotube; atomizing said mixture to form aerosol droplets; and, depositing the aerosol droplets on a sampling surface. In some embodiments, the analyte and matrix are in separate solutions prior to said mixing step. In some embodiments having analyte and matrix are in separate solutions prior to said mixing step, the separate solutions are both aqueous solutions.

In another embodiment of the present invention, there is a method for the laser desorption of analyte molecular ions from a sample, comprising the steps of combining the analyte with a matrix which absorbs laser light, said matrix comprising a component selected from the group consisting of native fullerenes, derivatized fullerenes, native nanotubes, derivatized nanotubes, inorganic nanoparticles, and any combination thereof; and, irradiating said combined analyte and matrix with said laser light. In some embodiments, the laser light comprises pulsed laser light. In some embodiments, the pulsed laser light comprises pulsed laser ultraviolet light. In some embodiments, the pulsed laser light comprises pulsed visible light or pulsed infrared light. In some embodiments wherein the analyte is combined with a matrix and irradiated, the light is from a continuous radiation source. In some embodiments using a continuous radiation source, the continuous radiation source has emission in one or more of the X-ray, UV, visible, or IR spectral regions. In some embodiments using a continuous radiation source having emission in one or more of the X-ray, UV, visible, or IR spectral regions, the emission is chopped mechanically, electro-optically, or both. In some embodiments wherein the emission is chopped mechanically, electro-optically, or both, the emission is chopped into time packets spanning 500 nanoseconds to 2 microseconds.

In some embodiments, there is a method for the laser desorption of analyte molecular ions from a sample, comprising the steps of combining the analyte with a matrix which absorbs laser light, the matrix comprising a component selected from the group consisting of native fullerenes, derivatized fullerenes, native nanotubes, derivatized nanotubes, and any combination thereof; and, irradiating the combined analyte and matrix with pulsed radiation from a synchrotron spanning wavelengths of electromagnetic radiation from UV to x-ray.

In some embodiments, there is a method for the desorption of analyte molecular ions from a sample, comprising the steps of combining the analyte with a matrix which absorbs radiation; and, irradiating said combined analyte and matrix with radiation having energy just above the ionization potential of the matrix. In some embodiments, the matrix comprises a native or derivatized fullerene, an inorganic nanoparticle, or a combination thereof. In some embodiments, the inorganic nanoparticle comprises metal. In some embodiments, the radiation is laser radiation.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

As used herein, the articles "a," and "an" signify both the singular and the plural and mean one or more than one.

As used herein, the term "analyte" is broadly defined as the species to be analyzed or determined and this includes such species alone or in combination with other components. This includes pure analytes with no other components present, and it also includes analytes present in a complex mixture such as a biological mixture. This latter example includes biological or non-biological analyte in a tissue sample.

As used herein, the term "derivatized" means chemically modified by the covalent or non-covalent coupling of organic functional groups such as carboxylic acids, alcohols, amines, esters, ethers, amide, aldehydes, ketones, nitriles, thiols, sulfide, sulfones, azides, anhydrides, alkyl, alkenyl, aryl; and inorganic functional groups such as phosphate, carbonate, and metals such as the alkali metal, the alkaline earth metals, the transition metals, the lanthanides, and actinides. The chemical modification can also involve covalent and non-covalent coupling to a chemical moiety (wherein the chemical moiety contains more than one functional group.

As used herein, ES is an abbreviation for and is defined as electrospray and refers to an electrospray ion source. ESI is an abbreviation for electrospray ionization.

As used herein, IMS is an abbreviation for and is defined as ion mobility spectrometry. The abbreviation IM is defined as ion mobility and refers to a ion mobility cell, especially when it is used in conjunction with other analytical instrumentation such as mass spectrometry.

As used herein, the terms "irradiation", "irradiated", and "irradiating", mean contacting with an energy source, such as any form of electromagnetic radiation. Irradiation in this context typically results in other processes on the atomic level and the molecular level, such as desorption, absorption, ablation, etc.

As used herein, MALDI/IM/o-TOF is an abbreviation for and defined as a matrix assisted laser desorption ionization/ ion mobility/orthogonal time-of-flight mass spectrometer.

As used herein, IM/o-TOF is an abbreviation for and defined as an ion mobility/orthogonal time-of-flight mass spectrometer.

As used herein, MALDI is an abbreviation for and is defined as matrix assisted laser desorption ionization.

As used herein, MS is an abbreviation for and is defined as mass spectrometry.

As used herein, "nanoparticle" is a particle having dimensions of from about 0.1 nm to about 1000 nm. An "inorganic nanoparticle" is a nanoparticle comprising inorganic material.

As used herein, "protein" is defined to mean any chain of amino acids comprising two or more amino acids. This includes peptides and proteins.

As used herein, SIMS is an abbreviation for and is defined as secondary ion mass spectrometry.

As used herein, TOF is an abbreviation for "time-of-flight" and is defined as a time-of-flight mass spectrometer.

As used herein, o-TOF is a time-of-flight mass spectrometer having a flight tube arranged orthogonally to the separation axis of a preceding separation technique.

In the present invention, the need for co-addition of glycerol as in the MALDI method of Tanaka has been eliminated. A MALDI matrix comprising a native or derivatized fullerene, or a native or derivatized nanospecies such as a nanotube, is taught herein. In the case of derivatized fullerenes an nanotubes, by chemically derivatizing the surface of $C_{60}$ and other fullerenes (including, but not limited to $C_{70}$, $C_{76}$, $C_{84}$, etc.), and chemically derivatizing related structures such as the various nanotubes, with a chemical moiety, preferably an organic acid, organic alcohol or with other chemical functionalities, the light absorbing particle (e.g. the fullerene) and the ionizing functionality (e.g. organic acid, organic alcohol or other chemical moiety which donates $H^+$ or $Li^+$, $Na^+$, $K^+$, $Rb^+$, $Cs^+$) are integrated onto the fullerene surface which itself can also physisorb the molecular analyte. The present invention also encompasses the derivatization of inorganic particles for the same purpose. Thus the optical absorber, the ionizing medium, and the analyte are all together simultaneously when the matrix is irradiated with desorbing radiation. The "other chemical functionality" may be organic or inorganic. Chemically anchoring organic functional groups such as carboxylic acids, alcohols, amines, esters, ethers, amide, aldehydes, ketones, nitriles, thiols, sulfide, sulfones, azides, anhydrides, alkyl, alkenyl, aryl, onto size selected fullerenes is also possible as is the use of other particles besides fullerenes. Other groups known to those of skill in the art are also useful in the present invention. The conventional MALDI acid matrices may be used in the present invention by derivatizing fullerenes therewith. Illustrative but non-limiting examples include nicotinic acid, benzoic acid, pyrazinecarboxylic acid, vanillic acid, cinnamic acid, benzyl alcohol, phenol, and derivatives any one of these. Because the light absorbing species in the present invention is the fullerene, it is also possible to use derivatizing agents which do not absorb strongly, if at all. Thus, while the conventional examples listed above all have an aromatic moiety capable of significant UV absorption, the present invention incorporates the use weak UV absorbers such as aliphatic acids and alcohols. These include acetic acid, propionic acid, butyric acid, valeric, as well as ethanol, propanol, and butanol. These examples are merely illustrative and not exhaustive, and one of skill in the art would immediately recognize the numerous possibilities for derivatizing agents applicable in the present invention.

Additionally, other nanospecies may be used in place of, or in addition to, fullerenes and fullerene clusters. For example, carbon nanotubes, in particular, single-walled carbon nanotubes (SWNTs) may be used in the present invention. Like the fullerenes, these species may be derivatized for use in the present invention. Nanoparticles of other compositions may also be used. Inorganic nanoparticles are also useful. These include, but are not limited to metal or metal ion clusters. These may be pure metals or combinations of metal and may also include metallic compounds such as metal oxides, etc. Nanoparticles of titanium nitride, aluminum nitride, boron nitride, carbonitride, carbon boron nitride, any combination thereof. Other inorganic materials, known to one skilled in the art are also within the scope of the present invention. The above list is merely illustrative and not exhaustive and the skilled artisan is aware of other substitutions which are also within the scope of the present invention.

This approach has several advantages. The chemically functionalized fullerene adsorbs biomolecules or other desired analyte molecules from solution onto the surface of the fullerene such that the resulting complex comprises, for example in the case of protein analysis, the analyte peptide, the light adsorbing carbon structure, and the proton donating chemical functionality, all three of which are thus localized in the same place at the same time. The light absorbing carbon structure has the advantage noted by Tanaka of adsorbing light over a wide range of photon energies. Thus, the analyte peptide desorption can be enhanced at wavelengths including—but not restricted to—the 357 nm produced by nitrogen lasers. The absorption of a laser photon by the fullerene structure is extremely efficient compared to organic matrices because the fullerenes have a higher optical absorption cross section over a much broader wavelength range. Laser irradiation will result in high ionization efficiency of the molecular analyte adsorbed to such a derivatized surface. These same advantages are also realized in the analysis of other biomolecules, including, but not limited to nucleic acids, oligonucleotides, and constituent components. Additionally, the methods and materials taught herein are applicable to molecular entities outside of the biomolecule context such as synthetic polymers or small organic or inorganic molecules including pharmaceuticals. Finally, elemental species may also be used in the present invention.

Because both the optical absorption of the fullerene and nanospecies particle and the chemical adsorption of the biomolecular or molecular analyte on the surface of the derivatized fullerene and nanospecies are strong and because the ionizing chemical functionality may also be present on the surface as well, the laser desorption of the ionized molecular analyte is very efficient at laser powers lower than usually required when using the traditional organic acid matrices for the MALDI analysis. The ability to use lower laser power is thus one advantage of these matrices. Another advantage is that only a very small molar ratio between the derivatized fullerene matrix and the molecular analyte is required to achieve good analytical sensitivity for the adsorbed molecular analyte. Often when using organic acid matrices an analyst must use molar ratios of up to 10000:1 matrix/analyte. In contrast, when using derivatized particles such as fullerene for the matrix, adequate mass spectra may be obtained from mixtures having ratios of derivatized matrix/analyte as low as 1:100. Although the ideal range of matrix/analyte ratio is 100:1 to 1:100, lower ratios of matrix/analyte are possible. In other words, mass spectra can be obtained when using these derivatized fullerene matrices in the presence of large excess molar concentrations of the analyte. By contrast the use of the commonly used organic acid matrices usually requires a large molar excess of the matrix compared to the analyte.

Fullerene-based chemistry has been developing very rapidly in recent years; see R. Taylor, Lecture Notes on Fullerene Chemistry: A Handbook for Chemists, Imperial College Press: London, 1988. It has led to applications in multiple areas including electronic devices, sensors and polymers. Since there are simple ways to derivatize fullerenes and make the complexes water-soluble, multiple biological applications have appeared as well. Fullerenes typically provide a strongly adsorbing high surface area for other species such as hydroxyl groups or acid groups to provide a source of protons. This has the advantage of making fullerenes soluble in different solvents so that solutions of fullerenes with bio-molecules can be prepared prior to depositing as thin films for MALDI mass spectroscopy. The intimate mixture will be the optimum situation for proton transfer to the sample species during laser vaporization. Alternatively, preparation of hydroxylated fullerenes can be readily accomplished by treatment with a strong base or by sulfonation in oleum followed by neutralization with water. In addition to the smallest possible 60 carbon atom containing fullerene molecules, giant fullerenes with masses up to 10000 a.m.u. are also available. The more common fullerenes include $C_{60}$, $C_{70}$, $C_{76}$, and $C_{84}$.

The second necessary condition of the MALDI matrix performance—efficient absorption of the laser radiation—is satisfied by the optical properties of carbon clusters. Moreover, the advantage of carbon-based matrices is connected with the possibility of using longer wavelength excitation sources including visible range lasers. This opportunity, provided by the broad band absorption of fullerenes, as well as of some types of nanotubes and other types of elemental particles or compound particles, is very attractive and provides advantages to their use.

There are a number of other advantages that this new class of matrices possesses over conventional chemical MALDI matrices. Experimental data shows that very low relative amounts of matrix are sufficient to achieve good signals from biological samples; no recrystallization of the matrix is required; in case of acidic functional groups no additional components will be needed to decrease the pH of the solution to promote efficient ionization as it is often is often the case when using conventional organic matrices.

Finally, the biggest advantage lies in the potential absence (due to the large size of fullerenes and nanotubes) of the interference from the matrix signal in the low mass range, which can be an obstacle in case the analysis of some low mass analytes (such as aromatic drug molecules) or small biological or biological fragments molecules are desired. Moreover, both the high mass matrix interference and the low mass matrix interferences can be avoided if one is to use our newly demonstrated technique which combines Ion Mobility/Orthogonal Time-of-Flight Mass Spectrometer (IM/o-TOF) to form a superior MALDI mass spectrometer (Gillig et al.; see also copending U.S. application Ser. Nos. 09/798,032 and 09/798,030, expressly incorporated by reference herein), as shown schematically in FIG. 1. Gillig et al. have also combined Ion Mobility Spectrometry (IMS) with MALDI for analysis of peptides and other large molecules at femtomole loading. The IM/o-TOF (1), allows separation by IMS with a resolution of up to 50 on the basis of ion volume (shape) while retaining the inherent sensitivity and mass accuracy of orthogonal time of flight MALDI. In the technique of Gillig et al. the ion mobility separates laser desorbed ions according to their drift time determined by their charge to volume ratio. The second stage of the MS-MS system is the time-of-flight mass spectrometer with orthogonal extraction which provides continuous sampling of the ions transported through the mobility cell with mass resolution of up to 2500. A unique data acquisition electronics and software allows collection of the mass-volume information in 2D. The MALDI chamber (2) comprises a computer controlled X-Y stage (3). Valve (4) provides pumping and valve (5) provides a gas inlet. A sample modification beam (6) described in further detail herein, may be, among other things, a metal ion cluster beam, a laser desorption/ionization source, an electrospray source, or an generator and accelerator of ionized aerosols. The sample (7) is preferably a biological sample and resides on the X-Y stage (3). Laser (8) is used to desorb analyte from the sample (7). After desorption, the analyte ions enter the mobility cell (9) and are separated according to their ion mobility. Differential pumping occurs across regions (10) and (11) in order to lower the pressure from the relatively high pressures of the mobility cell (9) to the low pressures of the time-of flight mass spectrometer (12), the region of lower pressure (11) houses focusing lenses in order to improve throughput of ions into the mass spectrometer (12). Signals from the detector are processed by a series of components, including a pre-amplifier (13), a constant fraction discriminator (14), a time-to-digital converter (15), the signal then being fed into a computer (16). The a time-to-digital converter (15), is also in contact with a laser timing controller (17) which feeds a high voltage pulser (18).

Compared to conventional MALDI/TOFs, this instrument has the crucial advantage that the MALDI ions can be separated according to their mobility charge/volume ratio prior to the mass separation and thus minimizing spectral congestion. It allows performance of IMS/MS (Ion Mobility Spectrometry-Mass Spectrometry) by inducing fragmentation of selected parent ions to sequence unknown peptides. This cannot now be efficiently done in currently available MALDI/TOFs.

This instrument allows reexamination of unusual materials that have historically been excluded for use as matrix (such as porphyrins and other higher mass light adsorbing structures) because of the introduction of isobaric mass interferences. As previously noted, isobaric interferences from the particle matrix has been one of the major reasons that the technique developed by Tanaka has not been more widely used. By using MALDI/IM/o-TOF, however, the shape of the matrix ions may often be quite different than the molecular analytes such as peptides or proteins, and thus, isobaric masses are separated on the basis of mobility drift time before entering the mass spectrometer. The surface modified fullerenes will be only the first of such new nanoparticulate MALDI matrix types made possible by the new MALDI/IM/o-TOF.

In addition to the smallest fullerene ($C_{60}$), it is possible to use larger size fullerenes and nanotubes such as single walled nanotubes (SWNT). Use of larger sizes of these clusters will lead to different mechanisms of the large peptide/protein adsorption, which may in turn, provide enhanced desorption/ionization efficiencies.

There are several methods of the sample preparation using fullerene or nanotube based matrices. In one embodiment, the matrix solution or suspension is premixed with the analyte solution and then deposited on a MALDI target, similarly to a conventional dried droplet method used for chemical acid matrices. Alternatively, the matrix solution or suspension is deposited on top of the analyte, which has been previously deposited on the target either in form of solution, tissue slice, or impacted in form of aerosol particles. In yet another approach, the matrix can be deposited first, and the analyte incorporated second in form of particles or solution that is subsequently dried. As a variation of the latter method, which implies simple adsorption and aggregation of the matrix on the target, the derivatized carbon matrix can be deposited to form specific chemical attachment to the surface in order to obtain more controlled coverage, and thus provide reproducible and spatially uniform signal from the analyte.

In another approach, the carbon matrix can be deposited by using an electrospray (ES) source. One can expect that $C_{60}$-based matrix compounds are more likely to remain intact during ES ionization since it occurs in a liquid phase. We can install a separate mobility cell with a time gate after the ES source in order to purify the ion beam and obtain a single component source.

In yet another approach, the matrix can be co-deposited with the analyte by aerosolization of the mixture solution and impacting the aerosol onto a standard stainless MALDI sampling plate surface. First, solutions (preferably aqueous) of analyte and matrix are mixed and atomized by using a collision atomizer to form a few micrometer droplets of the solution. The droplets can be then introduced to a flow tube where a flow of ultra-high purity gas promotes water evaporation in the droplets. Since both analyte and matrix are involatile they remain in the droplet during drying. Solid particles with the desired mixture of the matrix and analyte are formed after complete drying. The composition in each atomized droplet is thus the same as in the solution. The aerosolized solid matrix/analyte particles are deposited onto a stainless steel MALDI sample plate by directing the gas stream onto a stainless steel MALDI plate. This way very uniform spatial distribution and intermixing of matrix and analyte molecules can be achieved. The solutions of matrix or analyte or both, may also be buffered. While it is preferred that the matrix and analyte be in separate solutions prior to mixing, they may be mixed outside of solution and then put into solution already as a mixture.

Fullerene-based materials can be beneficial in cases when the interference from the matrix should be avoided, or where thorough mixing and co-crystallization of matrix and analyte is either not desirable or impossible. For example, depositing a monolayer coating of the derivatized $C_{60}$ onto a biotissue sample will provide a significant advantage for molecular analysis from such intact biological structures. The use of an electrospray source with time gated mobility cell, so that a purified ion beam provides a uniform coverage of the MALDI target, will allow for the depth profiling of complex biological samples, such as tissues. Once the top layer containing the matrix is desorbed and analyzed, a new layer of carbon clusters is deposited, and thus a new tissue layer can be analyzed. Due to much stronger radiation absorption of carbon clusters, this process can be performed without a significant damage to the underlying layers. This technique will have significant advantages over currently employed methods that utilize conventional chemical matrices and require dissolution of biological material in the solution containing the conventional matrix that is spotted on top of the tissue. Use of conventional prior art methods significantly limits the variety of molecules that can be analyzed due to the solubility, and excludes the possibility of fine depth profiling.

The data acquisition for the 3D tissue imaging proceeds by the following steps of 1) adding a dispersed thin layer of matrix, 2) acquiring 2D spatially resolved mobility resolved mass spectra by moving a focused laser beam from spot to spot until all the added matrix has been ablated 3) storing the spatially resolved mobility resolved mass spectra in a computer, 4) and repeating steps 1-3 until a desired amount of material has been removed. This sequence is shown schematically in FIG. 2. Initially, in situ deposition of the derivatized particle matrix is performed uniformly over the desired area of the tissue sample surface. A nitrogen laser for example is then focused precisely to a 20 µm diameter point (located at x and y) on the sample surface and pulsed to produce a spatially localized MALDI/Ion Mobility/o-TOF mobility/mass spectrum. Copending patent application Ser. No. 10/155,291 describes a unique way of acquiring the MALDI/Ion Mobility/o-TOF mobility/mass spectrum. The top diagram illustrates the expanded timing sequence used to acquire a two-dimensional Ion Mobility Time vs. Mass spectrum. The timing of consecutive o-TOF extraction pulses is offset slightly with respect to each individual laser pulse (all under computer control) to increase the effective mobility resolution that would otherwise be limited by the extraction period of 100 µs in the figure. This interleaving of the extraction pulses with respect to the laser pulse results in 5 µs or better mobility time resolution. Also the use of specially designed multianode detectors (see copending application Ser. No. 10/155,291) can reduce the number of such interleavings and even further increase the mobility resolution for a given number of laser pulses.

Figure 2:
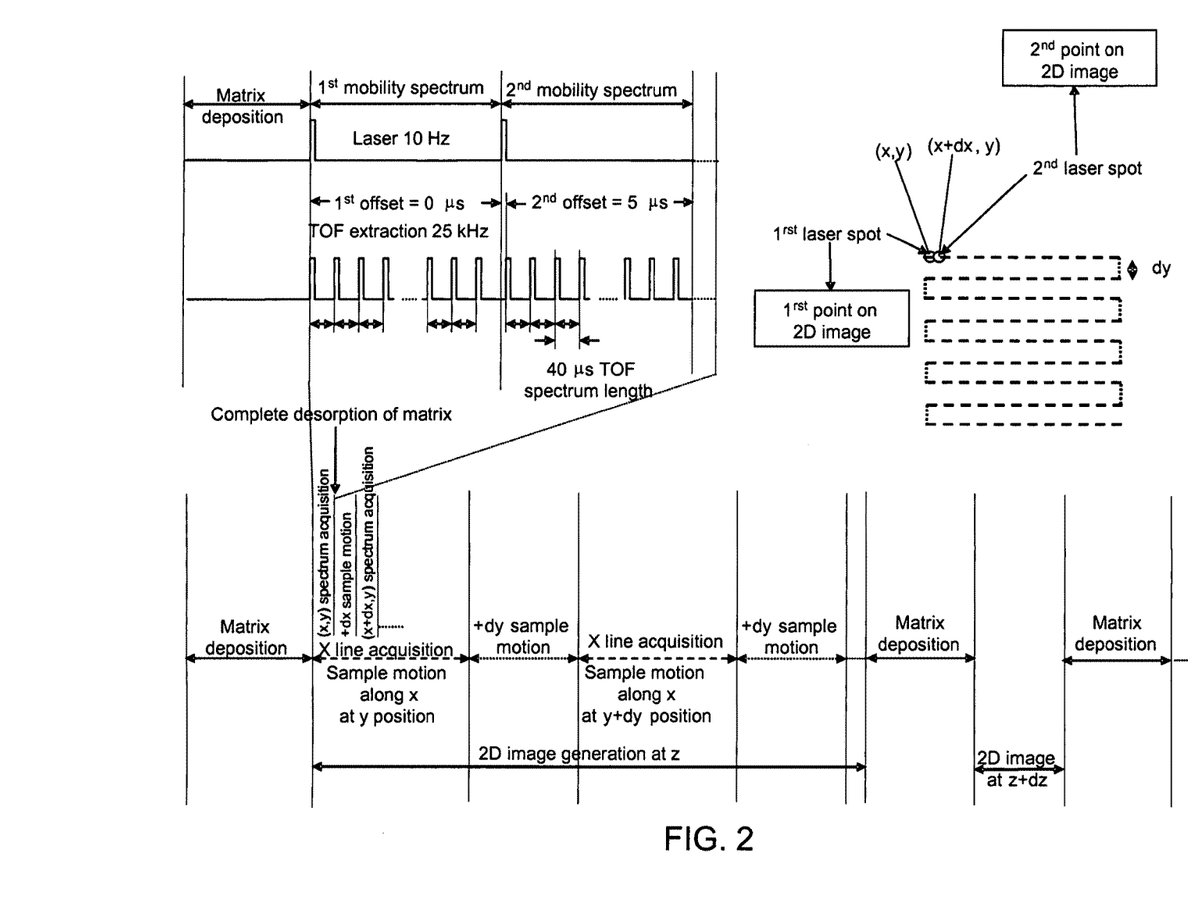
FIG. 2 is a schematic illustration of the data acquisition sequence for the 3D tissue imaging.

When the matrix material at a specific x-y position has been completely desorbed, which is determined either by signal loss or after a known number of laser shots, the sample is moved along the x direction to a point (x+dx, y). The laser spots at (x, y) and (x+dx, y) are preferably overlapping for oversampling and more complete area coverage. During the sample motion, the laser may be turned off. Successive sample motion along x axis/MS acquisition steps are iterated and yield a line image for the mobility drift time-mass region of interest. At the end of the line, the sample is moved along the y direction (dy). This laser rastering generates a 2D image of the top sample layer. A method to measure three dimensional distributions of molecular or elemental analyte within a sample ("molecular depth profiling") can be performed since the nanoparticulate matrix is so efficient and is spatially localized within the first few nanometers of the sample surface. Because the particulate matrix is so spatially localized, a desorption laser wavelength and power can be chosen so that optical adsorption is almost exclusively within the nanoparticulate and thus only the top-most few nanometers of nanoparticulate matrix and analyte are removed. Upon complete desorption of the nanoparticulate matrix, laser desorption stops, and the nanoparticulate matrix must be reintroduced again. For depth profiling the sequence of matrix deposition/2D image acquisition sequence is repeated. From the separately stored images a 3D picture of the spatial molecular distributions can be reconstructed.

Acquisition of the MALDI/IM/o-TOF mobility resolved mass spectrum at each laser spot should be under computer control. The entire MALDI/IM/o-TOF mobility resolved mass spectrum could be saved at each location or alternatively the computer could be programmed to select marker biomolecules at specified mobility drift time and mass in real-time. Alternatively, with acquisition parameter control, a larger predefined region of the MALDI/IM/o-TOF mobility resolved mass distribution is acquired and integrated followed by a windowing of an area of mobility drift time and mass which is used to reduce the entire the MALDI/IM/o-TOF mass resolved spectrum to a single intensity number associated with each x-y sample position. This could reduce the size of the data sets at each x-y point on the surface when the spatial distribution of a few known molecules of interest is desired. Once a particular method of data reduction of the MALDI/IM/o-TOF mobility resolved mass spectrum is chosen, the 3D distribution of molecules is created by successive steps of acquiring the 2D spatially resolved data, adding matrix, and repeating the next set of 2D spatially resolved data until the desired depth resolution has been achieved. A depth scale can be established by dividing the crater depth produced after laser desorption by the number of times the 2D spatial images have been acquired. The crater depth may be measured by many techniques known to those skilled in the art including but not limited to stylus profilometry, optical profilometry, or scanning atomic force microscopy. Alternatively, non-contact optical methods can be employed to measure the evolution of the crater depth as a function of the number of 2D images acquired.

Some common inorganic particles useful in the present invention include, but are not limited to, titanium nitride, aluminum nitride, boron nitride, carbonitride, carbon boron nitride, and any combination thereof. The inorganic particles may also comprise metal. In the case of metal this may be a metal cluster, preferably a finely divided metal cluster. Examples include, but are not limited to, gold, molybdenum, copper, copper lithium alloy, platinum, and any combination thereof.

For any of the possible matrices useful in the present invention, although any analyte species may be analyzed using the method, it is best suited for the analysis of biological analytes, including, but not limited to, proteins (such as antibodies, enzymes, and other proteins), nucleic acids and oligonucleotides. Lipids are also potential analytes for the method of the present invention. Other analytes, such as drugs and drug metabolites (including pharmaceutical drugs and illicit drugs of addiction) are also amenable to analysis using the method of the present invention. The analyte may also be a synthetic organic or inorganic polymer. It may be a herbicide, pesticide, or explosive.

Derivatization may include the covalent or non-covalent bonding of various chemical moieties to the matrix material. These chemical moieties include nicotinic acid, benzoic acid, pyrazinecarboxylic acid, vanillic acid, cinnamic acid, benzyl alcohol, phenol, acetic acid, propionic acid, butyric acid, valeric acid, derivatives thereof, and any combination thereof. Other examples of the chemical moieties include alcohols such as ethanol, propanol, butanol, isomers thereof, and any combination such alcohols. When the matrix components have acid and/or alcohol functionalities, they may be further functionalized with alkali metal ions. A quaternary amine (such as acetylcholine and ammonium hydroxide) may be attached y salt formation to the matrix. Biological molecules or portions thereof, such as proteins and epitopes may be used to derivatize the matrix material. One non-limiting example includes the derivatization with a biotin tag. Alternatively or additionally, derivatization may be accomplished using long chain fatty acids. Alternatively, enzymes, antibodies, specific sections of DNA, RNA or their complements, or combinations thereof, may be attached to the nanoparticulate surface to promote biologically specific binding to the so derivatized surfaces.

Although any form of radiation may be used to irradiate the analyte/matrix in the MALDI method of the present invention, laser light, and in particular pulsed laser light is preferred. Preferably, such laser light falls in the ultraviolet spectral region, but it may also fall in other spectral regions such as the visible or infrared spectral regions. The radiation may also be from a continuous source. Preferably, such a continuous source has emission in the UV, visible, or infrared regions of the electromagnetic spectrum, but it may also be from outside these spectral regions. The continuous radiation source may be chopped, either mechanically, or electro-optically, or both. When chopped, it is preferable that it is chopped into time packets spanning 500 nanoseconds to 2 microseconds. This can be particularly useful when the radiation is tuned just above the ionization potential of the nanoparticulate matrix to produce low (or zero) energy photoelectrons from the nanoparticulate surface which can enhance ionization of bioanalytes—particularly negative ion formation. Using these energetic tunable photon sources or alternatively a fixed wavelength of just sufficient energy to photoeject low energy electrons from the nanoparticulate matrix affords an excellent capability for producing analyte ions—particularly negatively charged analyte ions. This useful feature of the cluster matrices for enhancing ionization makes use of the broad and strong optical absorbance of the cluster when coupled with a laser wavelength (or multiphoton combination of wavelengths) which is just above the ionization potential of the cluster. When the adsorbate/cluster combination is irradiated with such an energy of photon (or photons) low (or even zero) energy photoelectrons can be produced from the cluster which will resonantly attach to the bioanalyte to form stable negative bioanalyte ions.

Another preferred form of radiation is pulsed radiation from a synchotron. Preferably, the method would used wavelengths from the ultraviolet region to the x-ray region.

EXAMPLES

The following examples are merely illustrative and not exhaustive. One of skill in the art, upon reading the examples would understand that the instrument and methods disclosed herein are applicable to other problems as well.

Equipment

Figure 1:
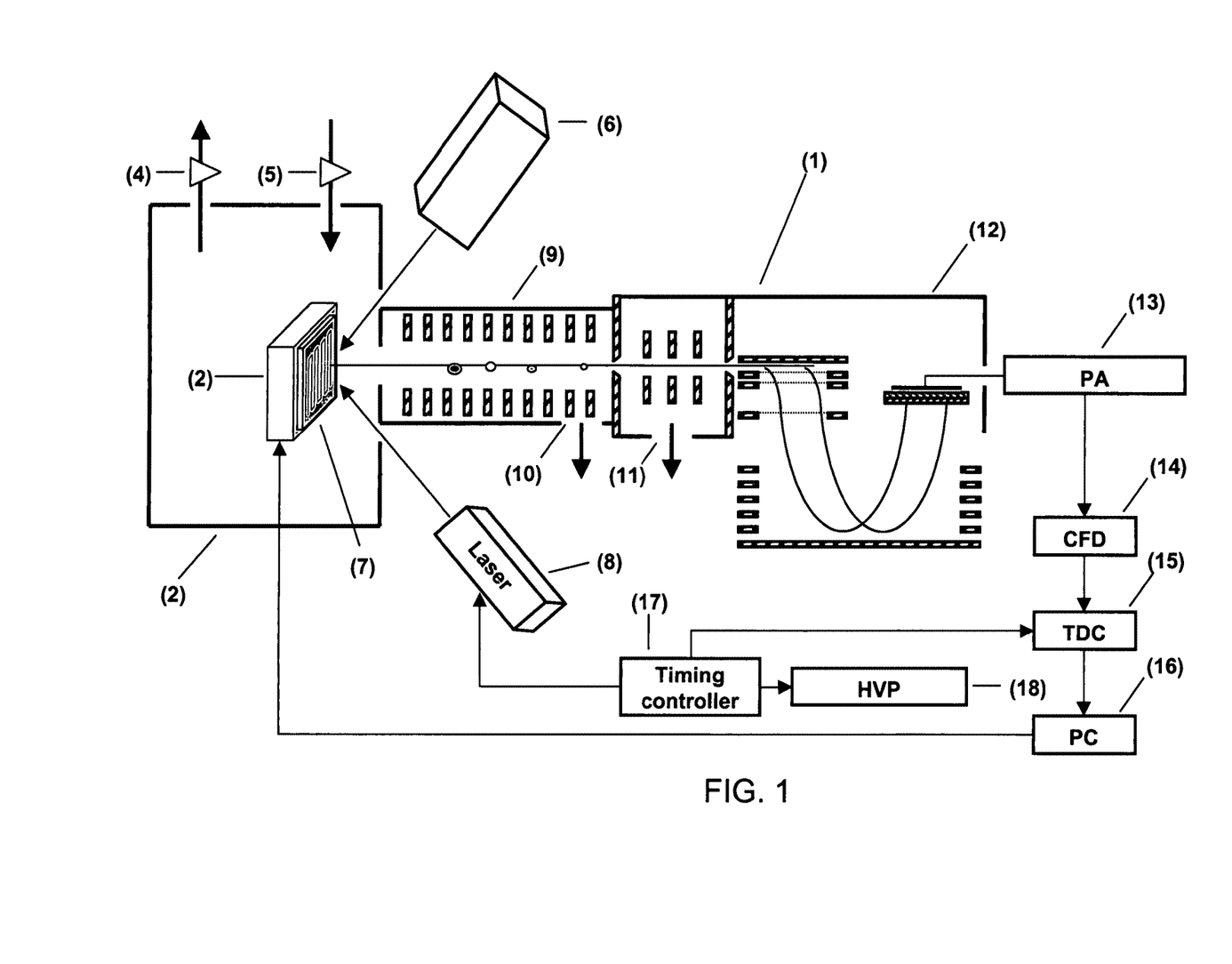
FIG. 1 is a schematic illustration of the MALDI-Ion Mobility/Orthogonal Time-of-Flight mass spectrometer.

The experiments were performed using two main installations: the Ionwerks MALDI/Ion Mobility/o-TOF and the Applied Biosystems VOYAGER SYSTEM 6101 high vacuum MALDI. The MALDI/Ion Mobility Spectrometer is schematically illustrated in FIG. 1.

Sample Analysis

A variety of peptide, lipid, and protein samples were analyzed. The MALDI targets were prepared using conventional dried droplet method. Due to generally low solubility of fullerene and nanotube matrices, their saturated solutions were produced by centrifuging the suspensions of particles in various solvents, including water, ethanol, chloroform, etc. In cases of particularly low solubility, fine suspensions of the materials were mixed with analyte or deposited on top of the spot containing dried analyte solution.

A series of functionalized fullerenes (derivatives of $C_{60}$) as matrices for peptides using both High Vacuum MALDI and MALDI/Ion Mobility techniques were tested. The tested compounds include $C_{60}((CH_2)_2COOH)_n$, $C_{60}(C_{11}H_{23})_n$, $C_{60}C_6H_5$, and others.

Example 1: $C_{60}((CH_2)_2COOH)_n$ as a MALDI Matrix for Peptides and Proteins

This compound has up to 6 attached chains (as shown by solid state NMR). This functionalized fullerene is only moderately soluble in water-ethanol (50:50) and water-acetonitrile (50:50) at levels of approximately 0.1 mg/ml, and has even poorer solubility in water. In solution it forms a strong acid with the pH of between 1 and 2.

MALDI data shows that the bonding is weak enough so that the complexes do not show up distinctively on spectra, most likely not surviving the laser desorption or transferring their charge to the analyte, so that a strong signal of a bare $C_{60}$ molecular ion is observed. The same result was obtained when using both direct laser excitation of the fullerene, or by premixing it with MALDI matrices such as CHCA and sinapinic acid.

However, the attachments still play a crucial role in the matrix performance; as pure $C_{60}$ does not work as a MALDI matrix, even if it is prepared using acidic media with similar chemical composition.

Figure 3:
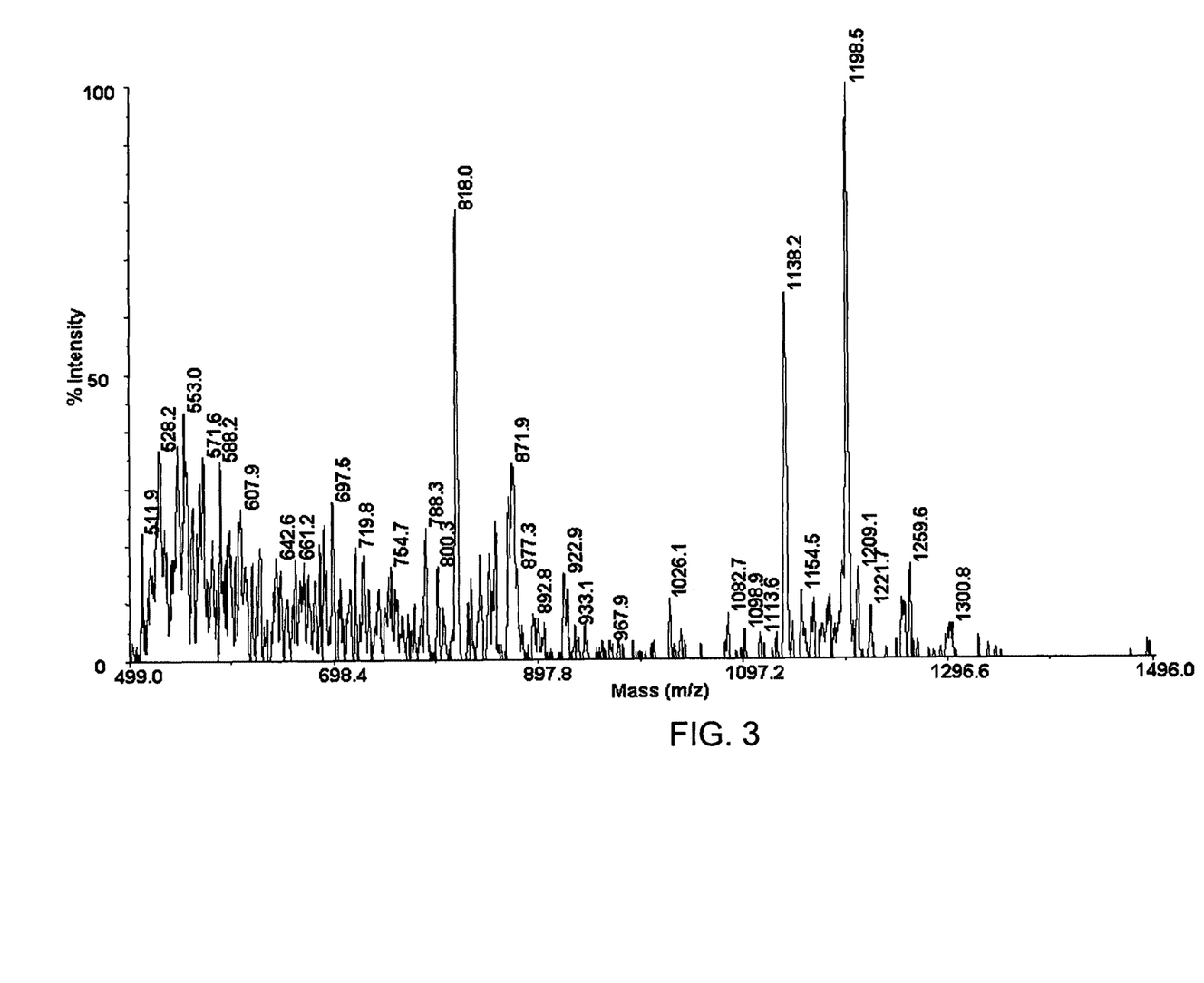
FIG. 3 is a typical HV MALDI spectrum of a mixture of three peptides.

Measurements have demonstrated that high quality mass spectra of peptides and proteins can be obtained even when using very low concentrations of derivatized matrix. This is in stark contrast to the results from the same peptide or proteins when analyzed by conventional MALDI in which large excesses molar concentrations of the small organic matrices relative to the analyte are required. FIG. 3 demonstrates a typical HV MALDI spectrum acquired using a derivatized matrix premixed with a solution of three peptides and deposited onto a MALDI target plate. Distinct peaks corresponding to M+H$^+$ ions are observed with good signal/noise ratio after only a few tens of laser pulses. It was found that in contrast to the case of conventional chemical matrices where high matrix/analyte concentration ratios are usually required, the situation is opposite for $C_{60}$ based matrices. It was determined that the best quality spectra—highest signal/noise ratio, low fragmentation and predominance of the M+H peaks compared to that of sodiated ions and potassiated ions—were routinely obtained at the matrix/analyte molar ratio between 1/1000 and 1/100. At higher matrix concentrations slightly higher peptide signal could be obtained, but the spectrum became more crowded, and sodiated ions became predominant. The sodium was determined to be an impurity in the peptide solution. Elimination of the alkali in the original solutions promotes the preferential formation of the M+H$^+$ ion even at the higher concentrations of matrix and peptide.

It was also determined that the ion signal only weakly depends on the peptide concentration in the low picomole range when the matrix/analyte ratio is below 1. This unusual dependence is likely due to the mechanism of the analyte-matrix attachment in solution, when only a certain number of peptide chains can be attached to one fullerene. In a large excess of the analyte, the higher peptide concentration does not lead to any increase in the ionization because the adsorption of peptide onto available derivatized fullerenes is saturated.

Likewise, a weak dependence of the signal upon the fullerene concentration can be explained either by the shortage of peptide (at high matrix/analyte ratio), or by a gentle character of the laser ablation which involves only the topmost monolayers of the sample (at high loads).

A comparison of the peptide signals when using standard matrices such as α-cyano-4-hydroxycinnamic acid (CHCA) and functionalized $C_{60}$ matrix was performed. While the latter was found to be less efficient than the chemical matrix, the carbon matrices and their performance are far from optimized. This includes both choices of functional groups, concentration ranges and sample preparation techniques.

Figure 4:
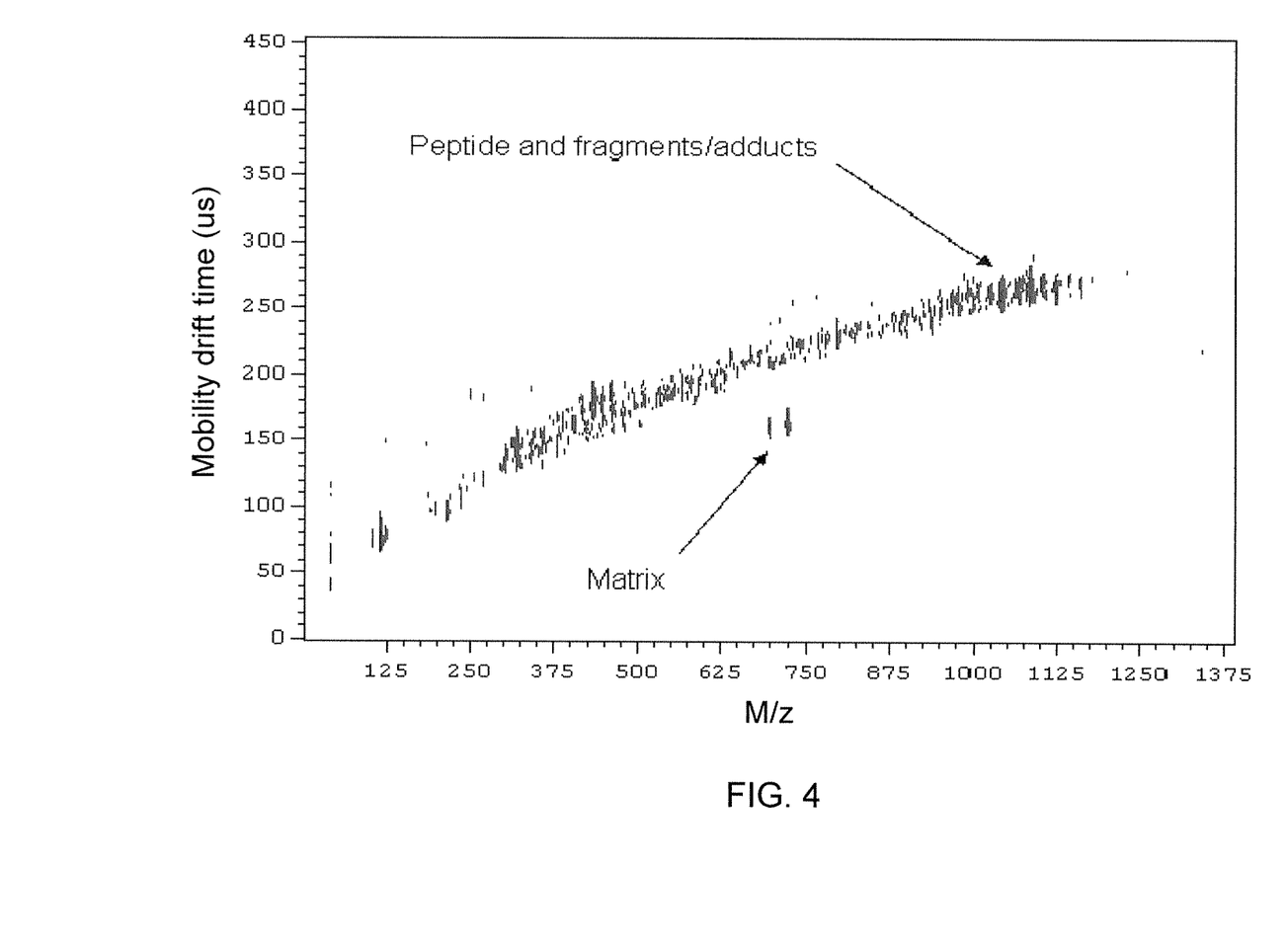
FIG. 4 is a 2D mobility-mass spectrum of angiotensin II with $C_{60}((CH_2)_2COOH)_n$ in water/ethanol solution used as a matrix.

Even in the case when the matrix signal is in the same mass range as the analyte signal, this hindrance can be overcome by using 2D mobility-mass spectra acquisition. FIG. 4 preliminary data from a sample prepared by the dried-droplet method of a mixture of angiotensin II and $C_{60}((CH_2)_2COOH)_n$ matrix. The ions of $C_{60}$ cluster and its higher mass derivatives are well separated by mobility from the angiotensin II parent ion and its fragments. In addition to the parent ion, there are minor ions also present at higher mass which are in part identified as M+K ions and other adducts. The data also shows that high mass proteins can be effectively analyzed using fullerene-based matrices.

Example 2: Carbon Matrices for Lipids

Figure 5:
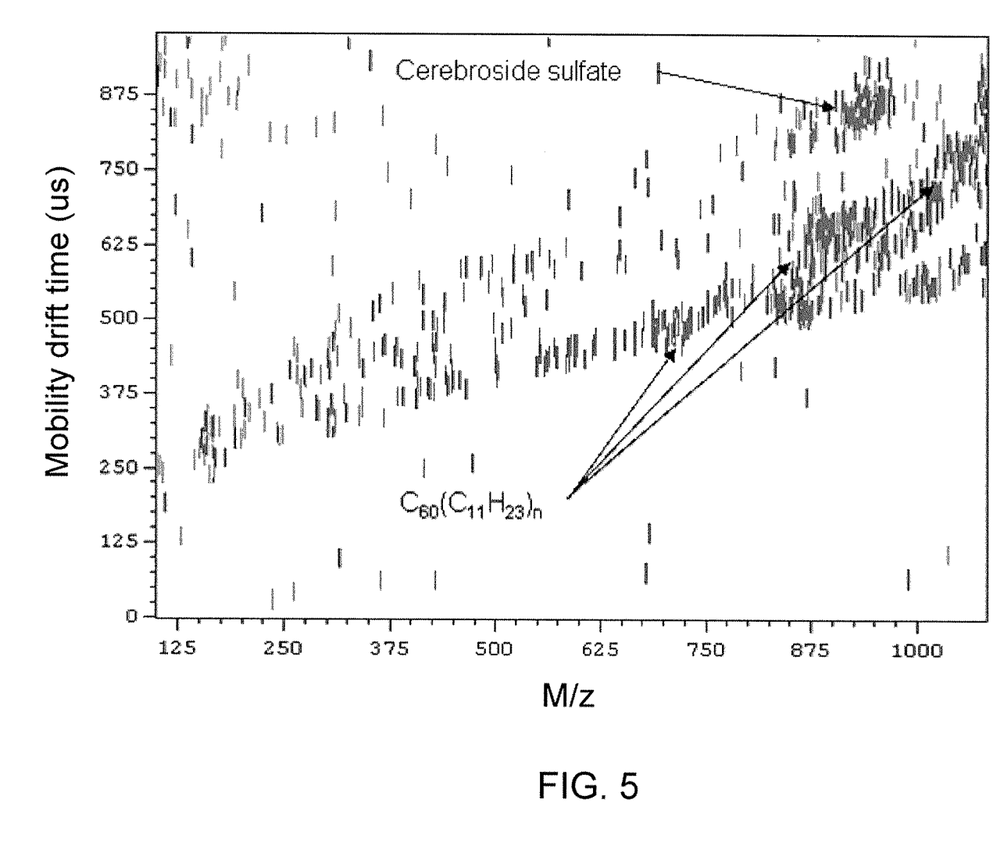
FIG. 5 is a 2D spectrum of cerebroside sulfate; $C_{60}(C_{11}H_{23})_n$ solution in chloroform was used as a matrix. Complexes with n=0, 1 and 2 are visible.

The use of non-water solution-based derivatized fullerenes as MALDI matrices for non-water soluble molecules such as lipids was tested. A saturated solution of $C_{60}$ $(C_{11}H_{23})_n$ in chloroform was used to obtain a test mobility-mass spectrum of cerebroside sulfate (FIG. 5, the instrument operating in low resolution mode). The nature of the 2D plot allows the easy separation of the lipid signal from that of the matrix. Although the fullerene that was used might not be the optimal choice since it can contain up to six $C_{11}H_{23}$ chains, the demonstrated feasibility of this approach to biomolecules other than peptides/proteins is apparent to one skilled in the art.

Example 3 Carbon Nanotubes

Figure 6:
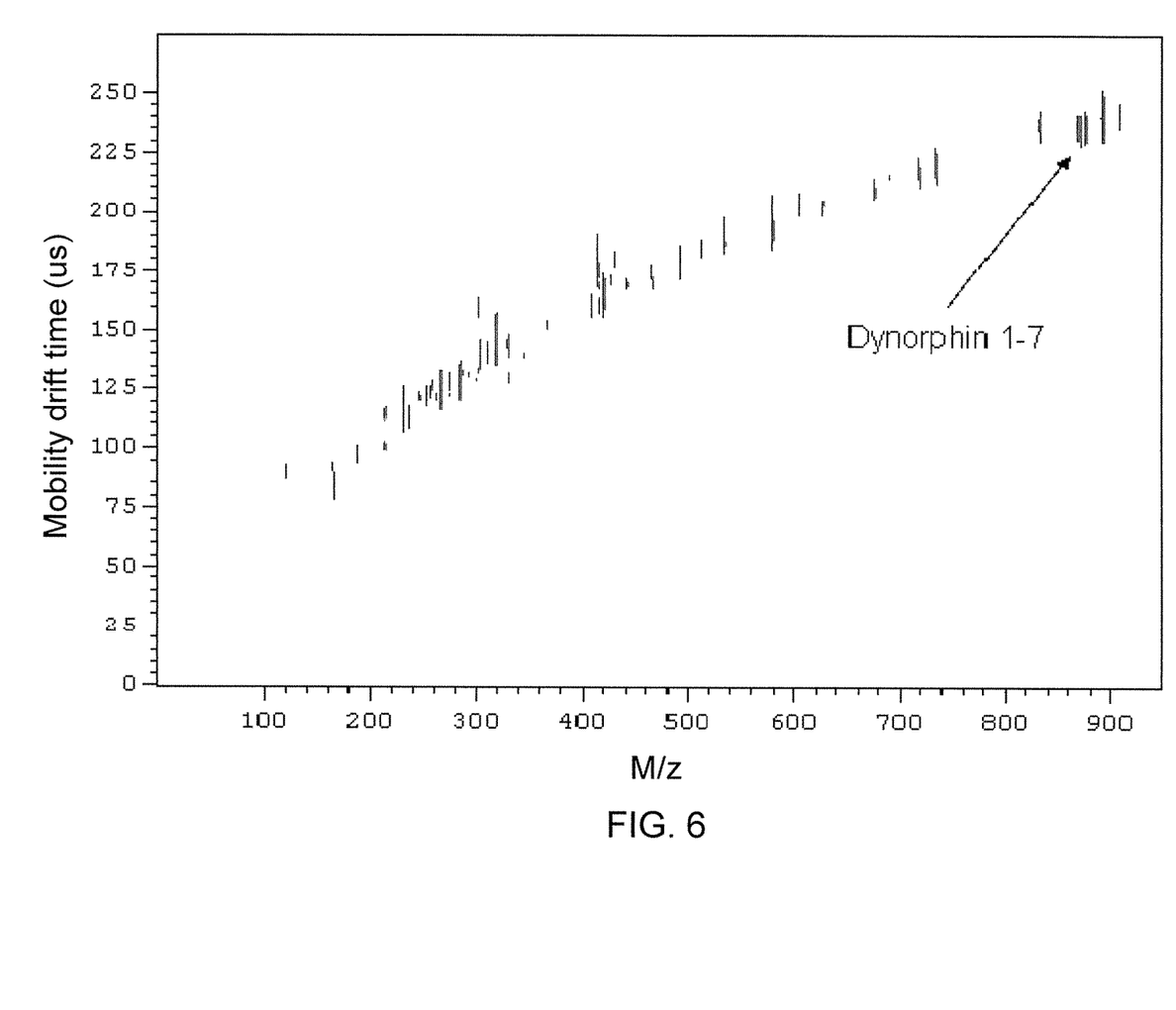
FIG. 6 is a 2D spectrum of dynorphin 1-7; single wall nanotubes functionalized with acidic $(CH_2)_2COOH$ groups used as a matrix.

Experiments using functionalized carbon nanotube materials as MALDI matrices for small peptides were performed. Single wall nanotubes with attached acid groups such as —CH$_2$CH$_2$COOH were used in form of water suspension (the solubility of these functionalized SWNTs is very low). The samples were prepared by dried drop method combining equal amounts of the suspension and the peptide solution. It was found that functionalized nanotubes' performance as matrices is somewhat similar to that of fullerenes with similar functional groups. FIG. 6 shows a 2D mass-mobility plot of the sample containing dynorphin 1-7.

The similarity is both in the intensity of the peptide signals and the relative abundance of M+H and M+Na peaks. This suggests the similar ionization mechanism dominated by the presence of acidic adducts, and, probably, similar desorption mechanisms due to the optical absorption of these two carbon materials. The important advantage of the SWNTs is the absence of matrix signal in the wide range of ion mass due to very large size and relative stability of single nanotubes and low mass of acid adducts. Therefore there is only one trend line on the plot in FIG. 5 formed by the peptide and its adducts/fragments.

Example 4 Applicability of Derivatized Fullerenes to Tissue Analysis

The applicability of derivatized fullerene matrix to the analysis of tissues is demonstrated. Direct mass spectrometric analysis of native biological products and/or tissues is one of the exciting prospects in analytical biochemistry. Recent investigations on tissue imaging using MALDI are beginning to yield important molecular information in many areas of biological and medical research. MALDI imaging of peptides and proteins expressed in tumor and healthy tissue may reveal correlations between certain marker proteins/peptides and the disease state. However the uniform incorporation of organic MALDI matrix remains probably the greatest difficulty for a successful MALDI image analysis. Wet matrix treatment of the tissue sample surface suffers from inhomogeneous matrix crystallization. The spatial distribution of the targeted proteins can also be easily perturbed.

The use of new fullerene matrices or other nanoparticulate matrices offer significant advantages as an alternative method for homogeneous, non-destructive and uniform matrix incorporation into near-surface regions of bio tissues. Ionization of the nanoparticulate matrix may be by using laser ablation (with or without matrix), electrospray source, or aerosol generator/ionizer source (in which aerosol particles are generated by well known methods from solutions or fluidized particulates followed by ionization) each source of which may be used to directly implant the ionized nanoparticulate into the biosurface (e.g. tissue slices). Alternatively any of the ionized nanoparticulates may be injected into a mobility cell which is interposed between the sample ion source and the analyte surface. The mobility cell allows for selecting the ions or ionized particulates produced by the ionization source. Gating techniques can be used to mobility select only a certain size range of ions which are then deposited onto the sample surface. The energy of the ionized particulate can be manipulated by adjusting gas pressures and voltages between the exit of the mobility cell and the sample. In this way the energy can be tuned to soft land the particulate onto the top of the surface or, by increasing the energy, the particulate can be injected into the near surface layer. Thus upon transport through the mobility cell, they are cooled and soft-land onto the biological tissue sample (or other surface of interest). Of course this technique would work for other surfaces besides biological tissues and with other particulate matrices besides fullerene or other nanoparticulate including but not limited to gold or silver clusters, carbon or fullerene particulates, wide-bandgap nitrides, transition metal clusters, and any of these particulate which have been surface modified.

Figure 7:
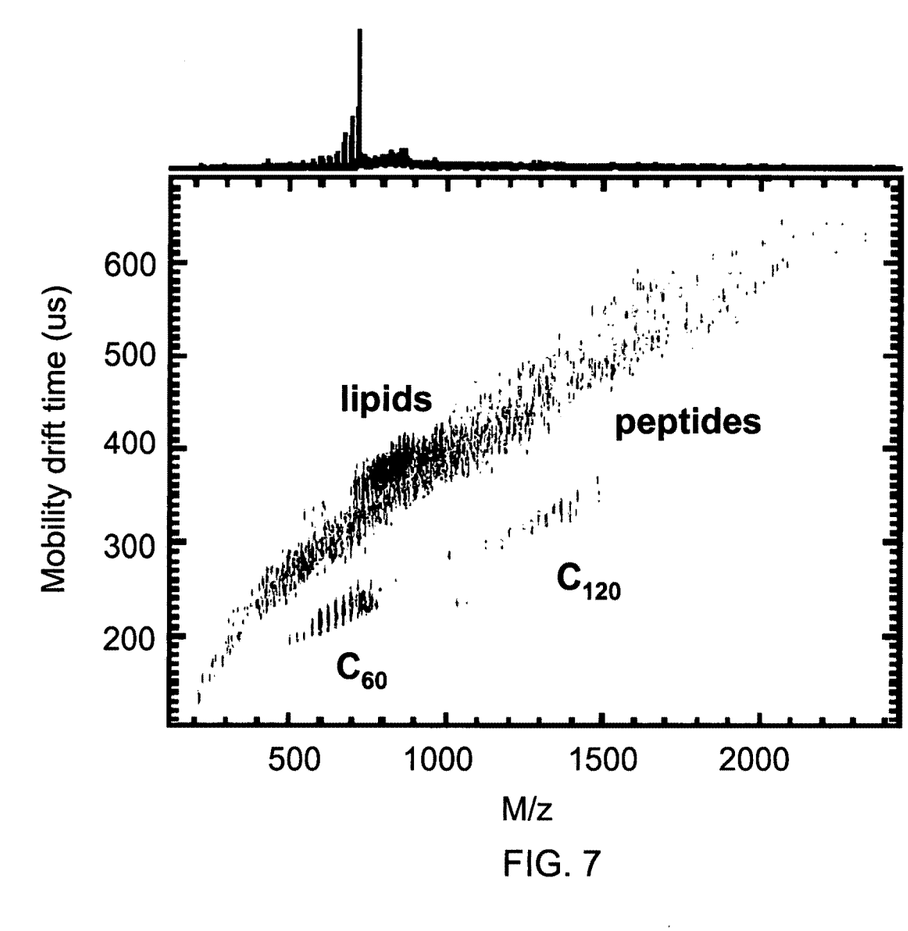
FIG. 7 is a 2D MALDI IM-TOF spectrum obtained from Srague Dawley rat brain tissue.

FIG. 7 shows the 2D MALDI IM-TOF MS spectrum obtained from Sprague Dawley rat brain tissue. The $C_{60}((CH_2)_2COOH)_n$ matrix solution was deposited on top of the prepared tissue slice and air dried. A good separation between the tissue lipids and peptides (corresponding trend lines are shown), as well as the matrix ion signals is observed. Thus the two major classes of brain tissue molecules which are resolved by mobility in FIG. 7 can be quickly and rigorously assigned to potassiated sphingomyelin and peptides based simply on their slope in the ion mobility-m/z chromatogram.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly; the appended claims are intended to include within their scope such processes, machines, manufacture, compositions of matter, means, methods, or steps.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

1. U.S. patent application Ser. No. 09/798,032, filed Feb. 28, 2001.
2. U.S. patent application Ser. No. 09/798,030, filed Feb. 28, 2001.
3. U.S. patent application Ser. No. 10/155,291, filed May 24, 2002.
4. Tanaka, K., Waki H, Ido Y, Akita S, Yoshida Y., Yoshida T., Rapid Commun. Mass Sectrom. 88, 2, (151).
5. Karas M., Bachman D., Hillenkamp F., Int J. Mass Spectrom. Ion Processes 1987, 78, (53).
6. Schurenberg M., Dreisewerd K., and Hillenkamp F., "Laser Desorptioin/Ionization Mass Spectrometry of Peptides and Proteins with Particle Suspension Matrixes," Anal. Chem. 1999, 71 (221-229).
7. R. Taylor, Lecture Notes on Fullerene Chemistry: A Handbook for Chemists. Imperial College Press: London, 1988.
8. K. J. Gillig, B. Rutolo, E. G. Stone, D. H. Russell, K. Fuhrer, M. Gonin, J. A. Schultz, "Coupling High Pressure MALDI with Ion Mobility/Orthagonal Time-of-Flight Mass Spectrometry," Anal. Chem. pp. 72, 3965, (2000).
9. A Study of Peptide-peptide Interactions Using MALDI Ion Mobility o-TOF and ESI-TOF Mass Spectrometry, A. S. Woods, J. Koomen, B. Ruotolo, K. J. Gillig, D. H. Russell, K. Fuhrer, M. Gonin, T. Egan and J. A. Schultz, J. Amer. Soc. Mass Spectr. 2002, 13, (166-169).

What is claimed is:

1. A method of preparing and analyzing a tissue sample comprising the steps of:
    combining the tissue sample with a matrix, said matrix comprising ionized inorganic nanoparticles wherein the combining step further comprises the step of injecting the matrix within a near surface layer of a slice of the tissue sample, wherein the near surface layer comprises a first few nanometers of the slice of the tissue sample, and,
    analyzing said combined tissue sample and matrix by laser desorption mass spectrometry.

2. The method of claim 1, wherein the inorganic nanoparticles are selected from the group consisting of nanoparticles of titanium nitride, aluminum nitride, boron nitride, carbonitride, carbon boron nitride, and any combination thereof.

3. The method of claim 1, wherein the inorganic nanoparticles comprise metal.

4. The method of claim 3, wherein said metal is selected from the group consisting of gold, molybdenum, copper, copper lithium alloy, platinum, and any combination thereof.

5. The method of claim 1, wherein the nanoparticles comprise silver clusters.

6. The method of claim 1, wherein the nanoparticles comprise at least one of gold clusters, wide-bandgap nitrides, and transition metal clusters.

7. The method of claim 1, wherein the injecting step comprises manipulating an energy of the ionized inorganic nanoparticles by at least one of adjusting gas pressures and voltages to inject the ionized inorganic nanoparticles into at least a near surface layer of the slice of the tissue sample.

8. The method of claim 1, wherein the tissue sample comprises an analyte.

9. The method of claim 8, wherein the matrix and analyte are combined in a ratio of matrix:analyte of from 10:1 to 1:10000.

10. The method of claim 8, wherein the matrix and analyte are combined in a ratio of matrix:analyte of from 1:1 to 1:1000.

11. The method of claim 8, wherein the analyte comprises protein.

12. The method of claim 11, wherein said protein comprises antibodies or enzymes.

13. The method of claim 8, wherein the analyte comprises a component selected from the group consisting of nucleic acids, oligonucleotides, any constituent components thereof, and any combination of the foregoing.

14. The method of claim 8, wherein the analyte comprises lipoproteins.

15. The method of claim 8, wherein the analyte is a lipid selected from group consisting of phospholipids, ceramides, derivatives thereof, and any combination of the foregoing.

16. The method of claim 8, wherein the analyte comprises a component selected from the group consisting of glycosylated proteins, glycosylated lipids, lipopolysaccharides, glycans, and any combination of the foregoing.

17. The method of claim 8, wherein the analyte comprises synthetic organic polymers, synthetic inorganic polymers, or both.

18. The method of claim 8, wherein the analyte comprises small organic molecules, organometallic molecules, or both.

19. The method of claim 18, wherein said analyte comprises a component selected from the group consisting of herbicides, pesticides, explosives, pharmaceutical drugs, and any combination thereof.

20. The method of claim 8, wherein the analyte is a drug of addiction.

21. The method of claim 20, wherein said drug of addition is selected from the group consisting of cocaine, morphine, heroin, amphetamine and derivatives thereof.

\* \* \* \* \*